United States Patent
Neidert et al.

(10) Patent No.: US 8,636,694 B2
(45) Date of Patent: Jan. 28, 2014

(54) MODULAR MEDICAL INJECTION SYSTEM

(75) Inventors: Michael R. Neidert, Minneapolis, MN (US); Kenneth C. Gardeski, Plymouth, MN (US); David F. Quinn, Galway (IE); Russell J. Redmond, Goleta, CA (US); Michael Collinson, Goleta, CA (US); Claude A. Vidal, Santa Barbara, CA (US)

(73) Assignee: Medtronic, Inc., Minneapolis, MN (US)

( * ) Notice: Subject to any disclaimer, the term of this patent is extended or adjusted under 35 U.S.C. 154(b) by 2450 days.

(21) Appl. No.: 10/867,059

(22) Filed: Jun. 14, 2004

(65) Prior Publication Data

US 2005/0277889 A1   Dec. 15, 2005

(51) Int. Cl.
*A61M 5/178* (2006.01)

(52) U.S. Cl.
USPC ............ 604/164.12; 604/164.01; 604/167.05; 604/167.06; 604/181

(58) Field of Classification Search
USPC ............ 604/164.01, 164.08, 164.12, 167.05, 604/167.06, 181, 187, 195, 196, 218, 221, 604/272, 523, 533
See application file for complete search history.

(56) References Cited

U.S. PATENT DOCUMENTS

| | | | |
|---|---|---|---|
| 5,092,853 A * | 3/1992 | Couvertier, II | 604/195 |
| 5,354,279 A | 10/1994 | Höfling | 604/164 |
| 5,364,374 A | 11/1994 | Morrison et al. | 604/272 |
| 5,573,520 A | 11/1996 | Schwartz et al. | 604/282 |
| 5,624,396 A * | 4/1997 | McNamara et al. | 604/93.01 |
| 5,728,149 A | 3/1998 | Laske et al. | 607/122 |
| 5,873,864 A | 2/1999 | Luther et al. | 604/280 |
| 6,197,016 B1 * | 3/2001 | Fourkas et al. | 604/537 |
| 6,309,375 B1 | 10/2001 | Glines et al. | 604/187 |
| 6,346,099 B1 | 2/2002 | Altman | 604/528 |
| 6,475,209 B1 * | 11/2002 | Larson et al. | 604/525 |
| 6,508,802 B1 | 1/2003 | Rosengart et al. | 604/523 |
| 6,591,129 B1 | 7/2003 | Ben-Haim et al. | 600/424 |
| 6,623,474 B1 | 9/2003 | Ponzi | 604/528 |
| 6,689,099 B2 | 2/2004 | Mirzaee | 604/107 |
| 6,689,103 B1 | 2/2004 | Palasis | 604/173 |
| 6,702,830 B1 * | 3/2004 | Demarais et al. | 606/159 |
| 2002/0143291 A1 | 10/2002 | Slater | 604/95.01 |
| 2003/0093059 A1 * | 5/2003 | Griffin et al. | 604/525 |
| 2003/0187396 A1 * | 10/2003 | Ponzi | 604/164.12 |
| 2004/0039338 A1 * | 2/2004 | Lee et al. | 604/164.12 |
| 2004/0172008 A1 * | 9/2004 | Layer | 604/533 |
| 2004/0193112 A1 * | 9/2004 | Glazier et al. | 604/164.1 |
| 2004/0249342 A1 * | 12/2004 | Khosravi et al. | 604/96.01 |
| 2004/0260241 A1 * | 12/2004 | Yamamoto et al. | 604/117 |
| 2005/0061329 A1 * | 3/2005 | Tran et al. | 128/831 |
| 2005/0137497 A1 * | 6/2005 | Wood | 600/562 |

\* cited by examiner

*Primary Examiner* — Emily Schmidt
(74) *Attorney, Agent, or Firm* — Carol F. Barry

(57) ABSTRACT

A medical injection system includes an elongate injection apparatus and an actuator apparatus. The actuator apparatus includes a fitting for coupling the actuator apparatus to a delivery catheter and a reversible gripping means to grip the injection apparatus; the gripping means is included in a plunger that is slideably engaged with the fitting and directs the injection apparatus through a fitting lumen and through a catheter lumen, when the fitting is coupled to the catheter.

25 Claims, 7 Drawing Sheets

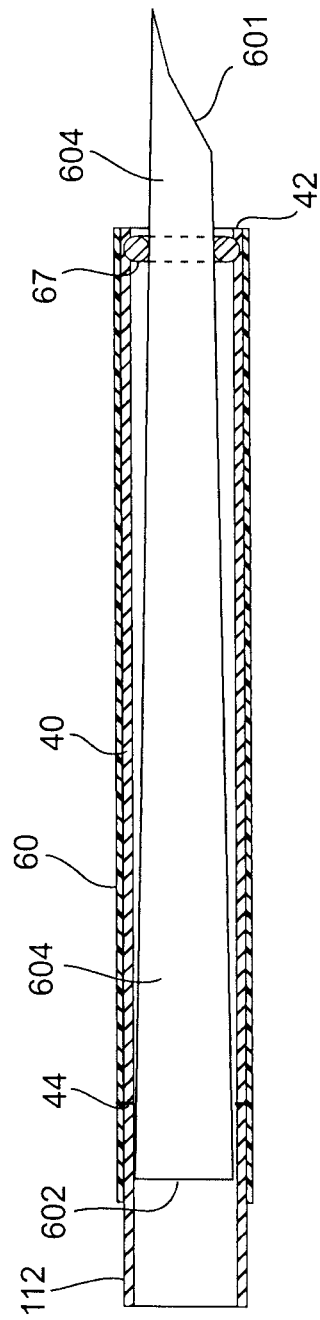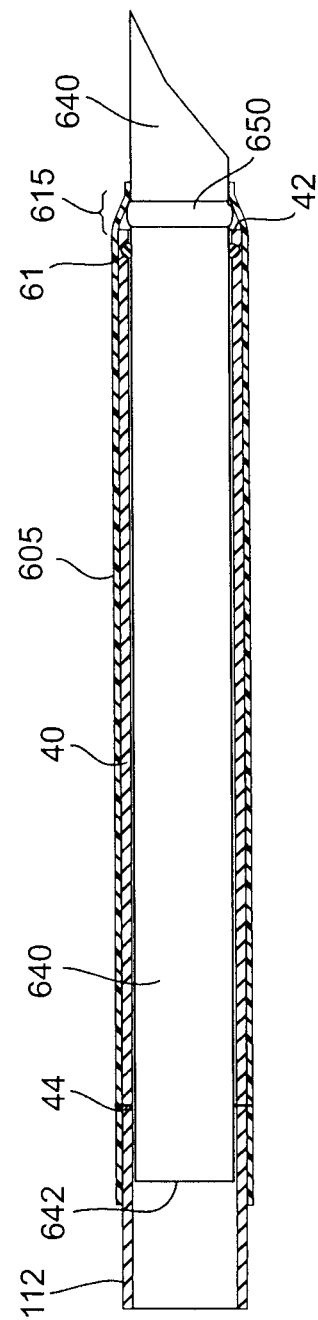

MODULAR MEDICAL INJECTION SYSTEM

TECHNICAL FIELD

The present invention relates generally to medical systems for delivering therapeutic agents and more particularly to elements of a modular injection system.

BACKGROUND

Because a therapeutic agent, for example pharmacological, genetic, or biological, may be ineffective or even toxic when delivered systemically, tools and methods for delivering therapeutic agents locally, that is, to a targeted tissue site, have been developed.

Many state-of-the art steerable catheters have lumens through which agents may be delivered. Rather than modifying state-of-the-art steerable catheter designs to integrally incorporate specific delivery mechanisms, such as means to inject agents into a tissue site, it is desirable to provide modular apparatuses, which can be coupled to any of such state-of-the-art steerable catheters and which include desired specific delivery mechanisms.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIGS. 6A-D are partial section views of distal portions of injection apparatuses according to alternate embodiments of the present invention.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
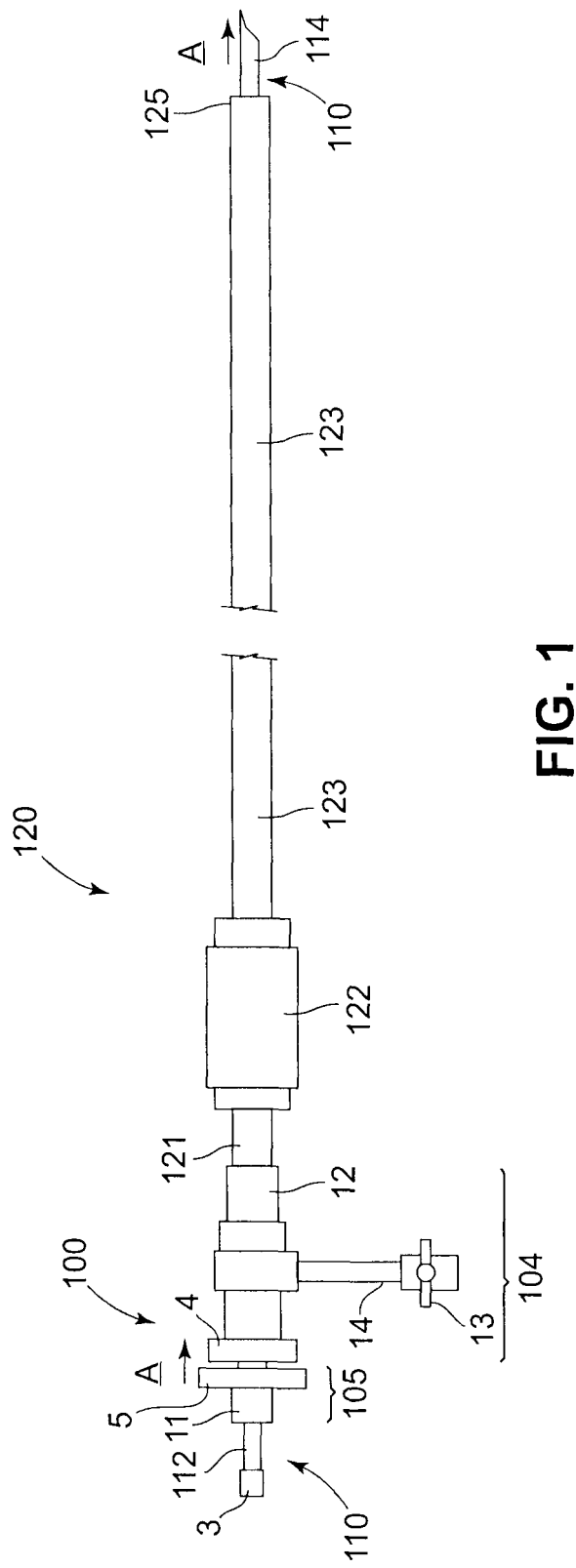
FIG. 1 is a plan view of a modular medical injection system according to one embodiment of the present invention.

FIG. 1 is a plan view of a modular medical injection system according to one embodiment of the present invention. FIG. 1 illustrates the system including a delivery catheter 120 to which an actuator 100 is joined by means of a coupling or connector 12 terminating a distal end of an actuator fitting 104; a lumen (not shown), which extends through a shaft 123 and a handle 122 of catheter 120 and through actuator 100, slideably engages an injection apparatus 110 whose needle tip 114 is shown extending out from a catheter distal end 125.

FIG. 1 further illustrates injection apparatus 110 including an elongate shaft 112 and a fitting 3 terminating a proximal end of shaft 112, fitting 3 being adapted to couple injection apparatus 110 to a source, for example a syringe, for injection of therapeutic agents from the source through a lumen 113 (FIG. 4) of injection apparatus 110. According to the illustrated embodiment, actuator 100 further includes a plunger 105 slideably engaged with fitting 104; plunger 105 includes a valve 11, for reversibly gripping shaft 112 of injection apparatus 110 so that when an operator forces plunger 105 toward fitting 104 per arrow A, shaft 112, being gripped by valve 11, is forced distally through catheter 120 so that needle tip 114 moves out from catheter distal end 125 to pierce a target tissue site in proximity to distal end 125. FIG. 1 further illustrates plunger 105 and fitting 104 each including radially extending surfaces 5 and 4, respectively, to facilitate operator handling to perform this operation.

According to embodiments of the present invention, catheter 120 may be any delivery catheter, known to those skilled in the art, that includes a compatible coupling for connector 12, for example a luer coupling; but catheter 120 is preferably selected from a group of steerable catheters known to those skilled in the art, for example those that would include manipulator means incorporated into a handle, i.e. handle 122 illustrated in FIG. 1, the manipulator means causing deflection of catheter shaft 123 to facilitate positioning of catheter distal end 125 at the target tissue site.

Figure 2:
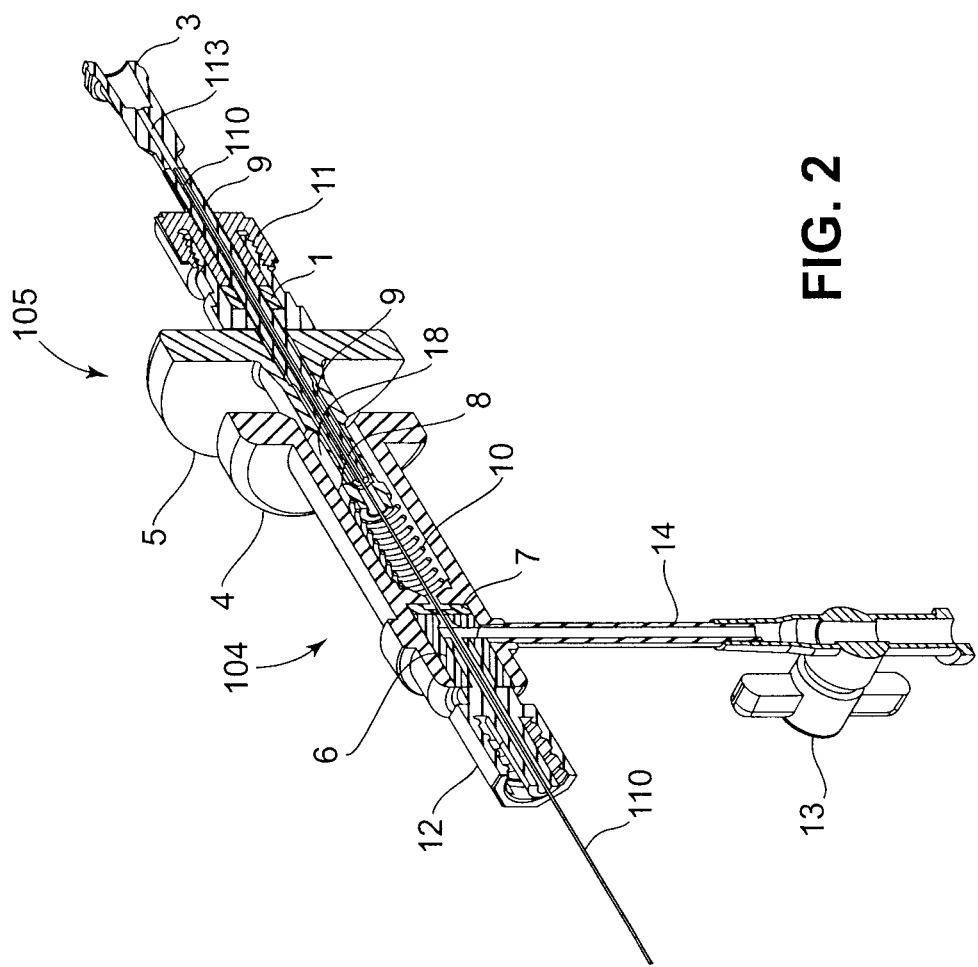
FIG. 2 is a perspective sectional view of an actuator apparatus and injection apparatus of the system shown in FIG. 1.

FIG. 2 is a perspective sectional view of one embodiment of actuator apparatus 100 and injection apparatus 110 of the system shown in FIG. 1. FIG. 2 illustrates injection apparatus 110 having been positioned within actuator apparatus 100 by passing needle tip 114 (FIG. 1) into opened valve 11, through lumens of plunger 105 and fitting 104, and then out through connector 12. According to an exemplary embodiment, molded rigid plastics, examples of which include polycarbonate, polyethylene and polypropylene, form plunger 105 and fitting 104.

FIG. 2 further illustrates fitting 104 including a spring member 10, which is mounted at an interface between plunger 105 and fitting 104, a side port 14, which is terminated by a stop cock 13 and in fluid communication with the lumen of fitting 104, for flushing a lumen of a catheter to which fitting will be coupled, and a septum 7, which is held in place by a septum cap 6, for sealing plunger 105 from the catheter lumen, while allowing passage of injection apparatus 110 therethrough. Septum 7 may be an elastomeric plug mounted within the fitting lumen. According to the illustrated embodiment, spring member 10 holds plunger 105 in a retracted position until a force is applied to slide plunger 105 distally with respect to fitting 104. When this force is applied, valve 11, which is illustrated here as a Touhy-Borst type, will have been tightened, according to means known to those skilled in the art, such that internal walls of a compressible member 1 protrude into the lumen of plunger 105 to grip injection apparatus 110 so that injection apparatus 110 is advanced distally along with plunger 105. It should be noted that the scope of the present invention covers other means for reversibly gripping injection apparatus 110 known to those skilled in the art, examples of which include, but are not limited to, 3-jaw chucks and set screws. FIG. 2 further illustrates injection apparatus 110 including a grip tube 9 positioned around shaft 112 (further illustrated in FIG. 4), which enlarges an outer diameter of shaft 112 to facilitate gripping of injection apparatus 110 by valve 11; grip tube 9 may further enhance gripping by means of a corrugated or soft and/or tacky outer surface.

Figure 3:
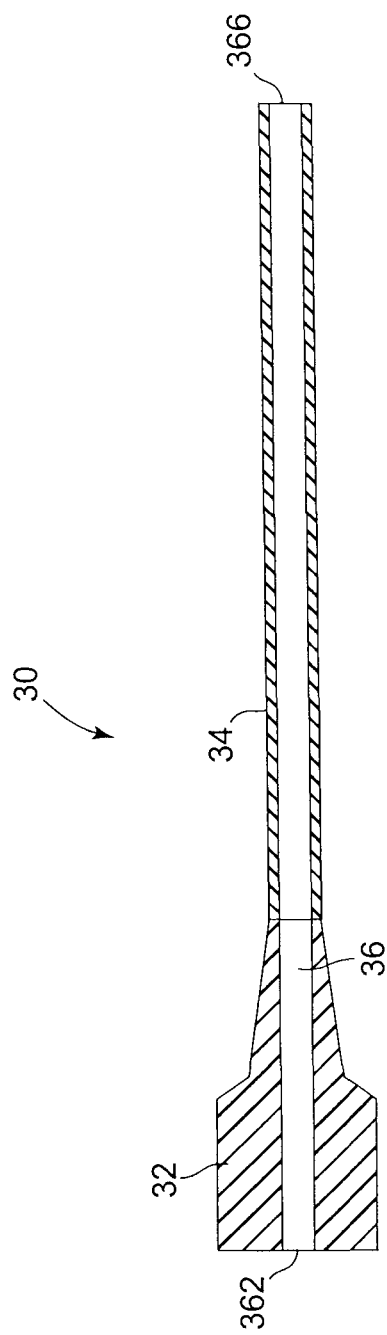
FIG. 3 is a section view of another member of a modular injection system according to one embodiment of the present invention.

According to one embodiment of the present invention, an introducer 30 as illustrated in section view in FIG. 3 is used to facilitate insertion of injection apparatus 110 through actuator apparatus 100. FIG. 3 illustrates introducer 30 including an introducer shaft 34 coupled to an introducer handle 32 and a lumen 36 extending through an entire length of introducer 30; according to one embodiment, a length of shaft 34 is sufficient to extend within actuator apparatus 100 from connector 12 through valve 11 (FIG. 2) so that lumen 36 may provide a smooth passage for injection apparatus 110 through an entire length of actuator 100. According to one method, a first end 366 of introducer 30 would be inserted into actuator 100 at connector 12 and passed through actuator 100 until first end 366 extends out from valve 11; then needle tip 114 (FIG. 1) would be inserted into lumen 36 at first end 366 and passed through until tip 114 protrudes from a second end 362 of introducer 30; finally introducer 30 would be removed from actuator 100 and fitting 104 may then be coupled to a catheter.

Returning now to FIG. 1, a method for advancing injection apparatus 110 through catheter 123, according to one embodiment of the present invention, will be described. Upon coupling actuator 100 to a proximal end 121 of the catheter 120, an operator may advance injection apparatus 110 through catheter 120 until needle tip 114 is approximately flush with catheter distal end 125, at which time valve 11 is closed to grip injection apparatus 110; thus, injection apparatus 110 is held in place within catheter 120 while the operator advances catheter 120 to a target tissue site. Once the operator has positioned catheter distal tip 125 in close proximity to the target site, the operator causes plunger 105 to advance distally, thereby pushing needle tip 114 of injection apparatus 110 into the site; either in conjunction with or following plunger action, a therapeutic agent is injected through injection apparatus 110 from a source of therapeutic agent which is coupled to injection apparatus 110, via fitting 3. According to the embodiment illustrated in FIG. 2, actuator apparatus 100 includes a stop in the form of a pin 8 extending into fitting 104 and interfacing with a depression 18 formed on plunger 105; the stop is designed to limit the plunger travel according to a prescribed injection depth. Finally, after injection of the therapeutic agent is completed, the operator allows plunger 105 to retract by means of the spring force previously described.

Figure 4:
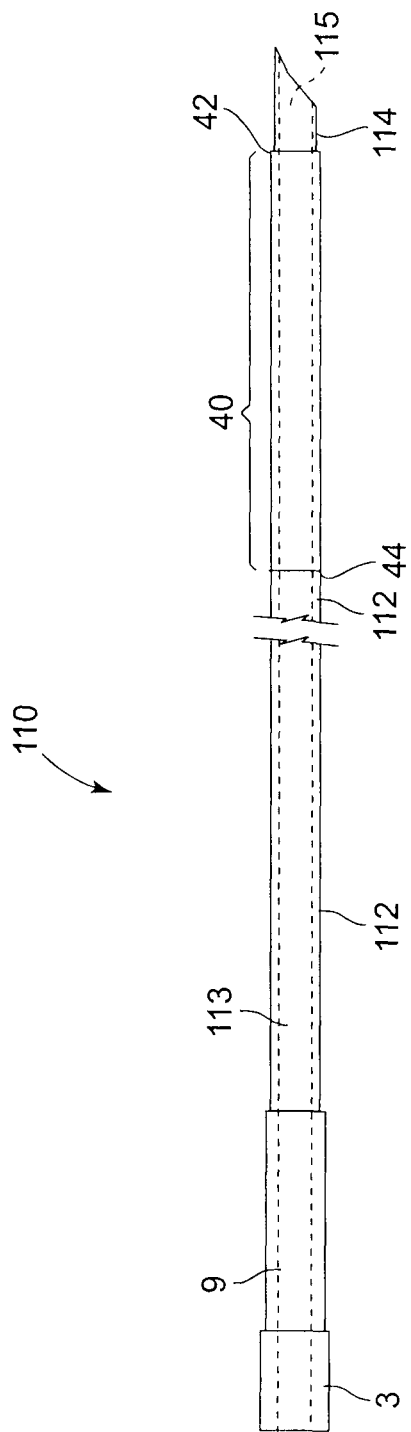
FIG. 4 is a plan view of the injection apparatus shown in FIG. 1 according to one embodiment of the present invention.

FIG. 4 is a plan view of injection apparatus 110 according to one embodiment of the present invention. FIG. 4 illustrates injection apparatus 110 including a modified distal portion 40 of shaft 112; distal portion 40 extends from an end 44 of a proximal portion of shaft 112 to a distal end 42 of shaft 112 and is modified for increased flexibility relative to the proximal portion of shaft 112. FIG. 4 further illustrates needle tip 114 extending from shaft distal end 42; according to some embodiments needle tip 114 is an independent member, which has been fixedly coupled to shaft 112 in proximity to distal end 42. Examples of appropriate needle tips include, but are not limited to, 20-25 gauge stainless steel tips.

Dashed lines in FIG. 4 indicate lumen 113 of shaft 112 extending from injection apparatus fitting 3 to needle tip 114 and approximately aligned with a lumen 115 of needle tip; lumens 113, 115 are adapted to deliver therapeutic agents out through needle tip 114 when tip 114 has been inserted into a target tissue site. Shaft may be formed from any appropriate biocompatible material known to those skilled in the art, which has sufficient strength and rigidity to accommodate lumen 113 and to push needle tip 114 into a target tissue site; one such material is stainless steel, for example 304 or 316L stainless steel. Because a pathway to a target tissue site may include a number of bends, which can be more acute closer to the target site, modified distal portion 40 decreases the inherent rigidity of shaft 112 over the length of distal portion 40 to improve tracking of injection apparatus 110 through catheter 120 to the target site.

Figure 5:
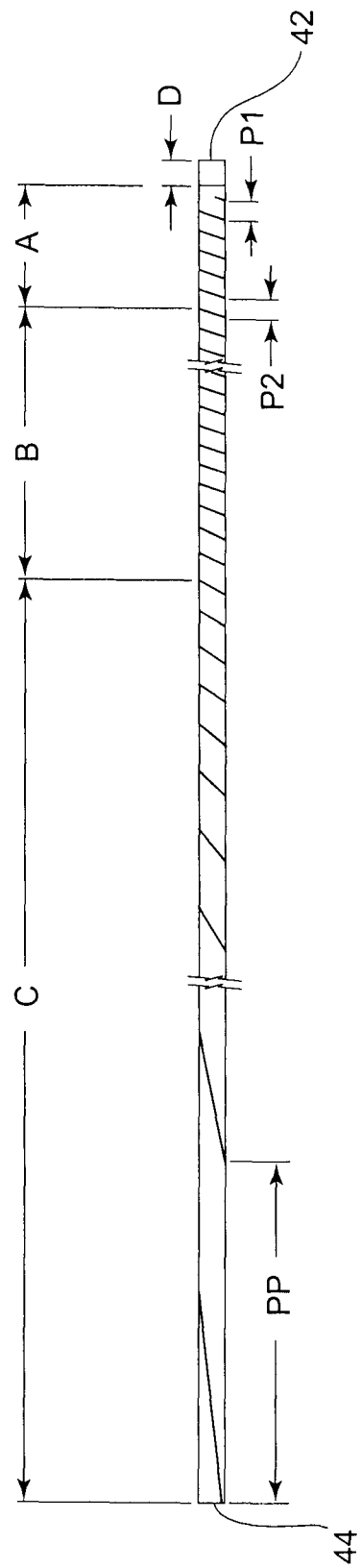
FIG. 5 is an enlarged detailed view of a portion of the injection apparatus shown in FIG. 4 according to some embodiments of the present invention.

FIG. 5 is an enlarged detailed view of distal portion 40 of injection apparatus 110 according to some embodiments of the present invention. FIG. 5 illustrates distal portion 40 including a spiral cut extending along segments A, B and C; according to the illustrated embodiment a pitch of spiral cut varies along portion 40 from a maximum or most proximal pitch PP to a minimum pitch P1. FIG. 5 further illustrates segment C having an exponentially decreasing pitch from end 44 distally, segment B having a constant pitch, segment A having a linearly decreasing pitch from P2 to P1, and a non-cut segment D terminating segment A. According to embodiments of the present invention, the spiral cut is formed through an entire wall thickness of shaft distal portion 40. Appropriate methods for making the spiral cut are known to those skilled in the art, one example of which is laser cutting, and, according to preferred embodiments, a kerf width is between approximately 0.015 mm and approximately 0.035 mm.

Examples of modified distal portion 40, included among embodiments of the present invention, are described in the following table:

|  | Segment C Wherein pitch is blended exponentially decreasing from ~4.9 mm to ~0.8 mm. | Segment B Wherein pitch is ~ constant. | Segment A Wherein pitch decreases linearly from ~0.75 mm to ~0.5 mm |
|---|---|---|---|
| Example 1 | Length ≅ 75 mm | Length ≅ 40 mm | Length ≅ 3.75 mm |
| Example 2 | Length ≅ 100 mm | Length ≅ 100 mm | Length ≅ 3.75 mm |
| Example 3 | Length ≅ 200 mm | Length ≅ 100 mm | Length ≅ 3.75 mm |
| Example 4 | Length ≅ 300 mm | Length ≅ 100 mm | Length ≅ 3.75 mm |

According to the exemplary embodiments, an overall length of injection apparatus 110 is approximately 150 cm and an outer diameter is between approximately 0.6 mm and approximately 0.7 mm.

Figure 6A:
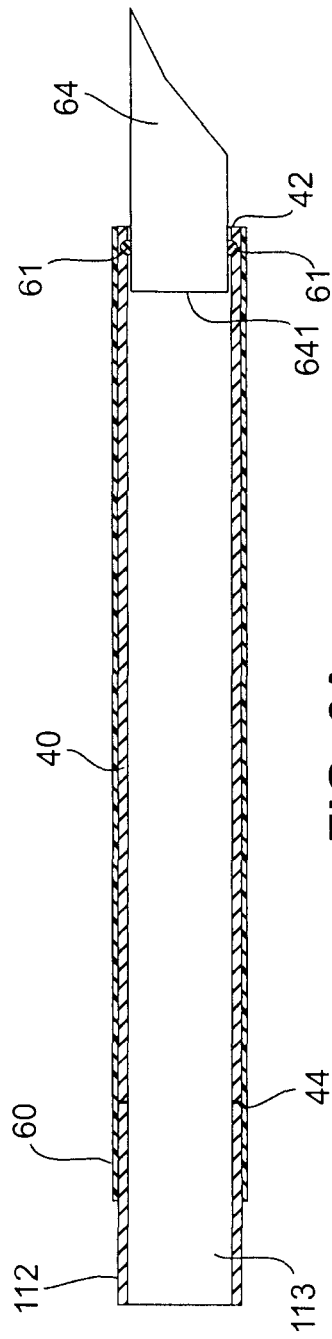
Figure 6B:
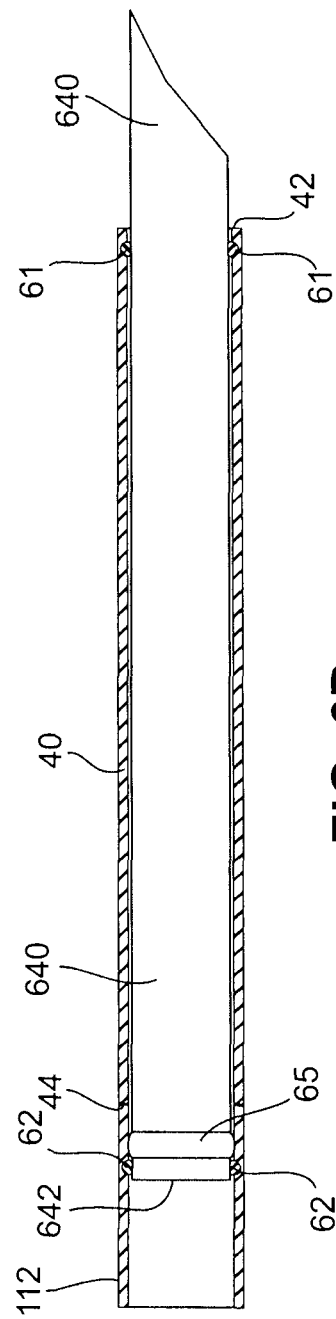

FIGS. 6A-D are partial section views of distal portions of injection apparatuses according to alternate embodiments of the present invention. FIG. 6A illustrates a needle tip 64 inserted into distal end 42 of shaft 112 such that a proximal end 641 is in proximity to distal end 42, while FIGS. 6B-C illustrate needle tips 640 and 604 that extend into shaft 112 beneath an entire length of distal portion 40 such that tip proximal ends 642 and 602, respectively, are positioned proximal to end 44. Needle tips 64, 640 and 604 may be formed of stainless steel, Nitinol, or any other appropriate needle material known to those skilled in the art.

According to the embodiment illustrated in FIG. 6A, needle tip 64 is fixedly coupled to shaft 112 by means of a joint 61, which may be formed by adhesive bonding, laser welding, mechanical crimping or any other suitable means known to those skilled in the art. FIG. 6A further illustrates an outer layer 60 formed about distal portion 40; according to the spiral cut embodiments, layer 60 prevents leakage of therapeutic agents out through the cuts. Outer layer 60 may be extruded over distal portion 40 or, in the form of a previously extruded tube, fitted over portion 40 and bonded in place, for example with an adhesive or by laser energy; examples of suitable materials for such outer layers include but are not limited to polyether block amides (PEBAX), polyurethanes, polyethylenes and silicones. According to alternate embodiments, outer layer 60 is a tube, which has been fitted over distal portion 40 and heat shrunk into relatively tight conformance with an outer surface of portion 40; examples of suitable materials for a shrink-fit outer layer include, but are not limited to, polyesters and fluoropolymers. One such exemplary embodiment incorporates a polyester shrink tube, available from Advanced Polymers of New Hampshire, having an inner diameter of approximately 0.029 inch and a wall thickness of approximately 0.00025 inch. FIG. 6B illustrates an alternate embodiment in which outer layer 60 is not included; rather a seal 65, for example made from silicone rubber, is positioned about an outer surface of needle tip 640, proximal to end 44, and engages an inner surface of shaft 112 to prevent passage of agents out through the spiral cuts of portion 40. FIG. 6B further illustrates needle tip 640 fixedly coupled to shaft by both joint 61 and a second joint 62.

FIG. 6C illustrates needle tip 604 tapering from proximal end 602 to distal end 601 wherein proximal end 602 is wedged within shaft 112. FIG. 6C further illustrates outer layer 60 formed about portion 40 and a joint 67 formed between needle tip 604 and shaft distal end 42. According to one embodiment, joint 67 solely fixedly couples tip 604 to shaft 112 and, according to another embodiment, joint 67 not only couples but further provides sealing between tip 604 and shaft distal end 42 (as illustrated by dashed lines), if proximal end 602 is not sealed within shaft. An adhesive backfill, a laser weld, or a mechanical crimp may form joint 67.

FIG. 6D illustrates an outer layer 605 extending over distal portion 40 and over a portion of needle tip 640 just distal to shaft distal end 42; layer 605 may be formed in any manner similar to those described for layer 60 and may be selected from the same group of materials. FIG. 6D further illustrates a seal 650 positioned between needle tip 640 and outer layer 605. A narrowing region 615 of the outer layer 605 extends over the seal 650 and engages the needle tip 640. It should be noted that shorter needle tip 64, illustrated in FIG. 6A could be incorporated into this embodiment as well.

In the foregoing detailed description the invention has been described with reference to specific embodiments. However, it may be appreciated that various modifications and changes can be made without departing from the scope of the invention as set forth in the appended claims.

What is claimed is:

1. A medical injection system, comprising:
   an elongate injection apparatus comprising:
   an elongate shaft including a shaft lumen extending from a proximal end of the shaft to a distal end of the shaft, a proximal portion extending distally from the proximal end, and a distal spiral cut portion extending distally from the proximal portion to the distal end of the shaft, the distal spiral cut portion comprising a first segment extending distally from the proximal portion, a second segment extending distally from the first segment, and a spiral cut extending along the first segment and second segment, the spiral cut having a generally exponentially decreasing pitch along the first segment and a generally linearly decreasing pitch along the second segment; and
   a needle tip coupled to the shaft and extending distal to the distal end of the shaft, the needle tip including a needle lumen extending therethrough and approximately aligned with the shaft lumen;
   wherein the shaft lumen and the needle tip lumen provide a passage for injection of therapeutic agents; and
   an actuator apparatus comprising:
   a fitting for coupling the actuator apparatus to a proximal portion of a delivery catheter, the fitting including a fitting lumen extending therethrough adapted to slidably receive the injection apparatus and to direct the injection apparatus through a lumen of the catheter; and
   a plunger slidably engaged with the fitting, the plunger including a plunger lumen extending therethrough adapted to slidably receive the injection apparatus and to direct the injection apparatus through the fitting lumen; the plunger further comprises means for reversibly gripping the injection apparatus within the plunger lumen;
   wherein the plunger slides distally and proximally with respect to the fitting to advance and retract, respectively, the injection apparatus within the catheter lumen when the actuator apparatus is coupled to the catheter and the gripping means grips the injection apparatus.

2. The system of claim 1, wherein the actuator apparatus further comprises an elastomeric plug positioned between the plunger and the catheter lumen, wherein the elastomeric plug seals the plunger from the catheter lumen while allowing passage of the injection apparatus.

3. The system of claim 1, wherein the actuator apparatus fitting further includes a side port in fluid communication with the fitting lumen for flushing the catheter lumen.

4. The system of claim 1, wherein the actuator apparatus fitting further includes a luer thread to couple with the catheter.

5. The system of claim 1, wherein the actuator apparatus further comprises a spring member mounted between the plunger and the fitting to hold the plunger in a retracted position until a force is applied to slide the plunger distally with respect to the fitting.

6. The system of claim 2, further comprising an introducer adapted for insertion through the fitting lumen and the plunger lumen of the actuator apparatus, the introducer including an adapter lumen extending therethrough to slidably receive the injection apparatus, and wherein the injection apparatus is loaded into the fitting lumen and the plunger lumen of the apparatus by means of the introducer, which is removed from the apparatus following loading.

7. The system of claim 1, further comprising an introducer adapted for insertion through the fitting lumen and the plunger lumen, the introducer including a lumen extending therethrough adapted to slidably receive the elongate injection apparatus, and wherein the elongate injection apparatus may be loaded into the fitting lumen and the plunger lumen of the apparatus by means of the introducer, which may be removed from the apparatus following loading.

8. The system of claim 1, wherein the distal spiral cut portion of the shaft of the injection apparatus further includes at third segment extending distally between the first segment and the second segment, the spiral cut having a generally constant pitch along the third segment.

9. The system of claim 1, wherein the injection apparatus further comprises an outer layer extending over the spiral cut portion.

10. The system of claim 9, wherein the outer layer has a wall thickness less than or equal to approximately 0.05 mm.

11. The system of claim 9, wherein the outer layer comprises a polymer.

12. The system of claim 8, wherein the distal spiral cut portion of the injection apparatus has a length between approximately 50 mm and 500 mm.

13. The system of claim 1, wherein the injection apparatus further comprises a grip tube positioned about the shaft in proximity to the shaft proximal end; the grip tube facilitating gripping by the means for reversibly gripping the injention apparatus within the plunger lumen.

14. The system of claim 1, wherein the injection apparatus further includes a fitting coupled to the proximal end of the shaft, the fitting adapted to connect the shall to a source for injection of the therapeutic agents from the source through the injection apparatus.

15. A medical injection system, comprising:
an elongate injection apparatus comprising:
an elongate shaft including a shaft lumen extending distally from a proximal end of the shaft to a distal end of the shall, a proximal portion extending from the proximal end, and a distal spiral cut portion extending distally from the proximal portion to the distal end of the shaft, the distal spiral cut portion comprising a first segment extending distally from the proximal portion, a second segment extending distally from the first segment, and a spiral cut extending along the first segment and second segment, the spiral cut having a generally constant pitch along the first segment and a generally linearly decreasing pitch along the second segment; and
a needle tip coupled to the shaft and extending distal to the distal end of the shaft, the needle tip including a needle lumen extending therethrough and approximately aligned with the shaft lumen;
wherein the shaft lumen and the needle tip lumen provide a passage for injection of therapeutic agents; and
an actuator apparatus comprising:
a fitting for coupling the actuator apparatus to a proximal portion of a delivery catheter, the fitting including a fitting lumen extending therethrough adapted to slidably receive the injection apparatus and to direct the injection apparatus through a lumen of the catheter; and
a plunger slidably engaged with the fitting, the plunger including a plunger lumen extending therethrough adapted to slidably receive the injection apparatus and to direct the injection apparatus through the fitting lumen; the plunger further comprises means for reversibly gripping the injection apparatus within the plunger lumen;
wherein the plunger slides distally and proximally with respect to the fitting to advance and retract, respectively, the injection apparatus within the catheter lumen when the actuator apparatus is coupled to the catheter and the gripping means grips the injection apparatus.

16. The system of claim 15, wherein the actuator apparatus further comprises an elastomeric plug positioned between the plunger and the catheter lumen, wherein the elastomeric plug seals the plunger from the catheter lumen while allowing passage of the injection apparatus.

17. The system of claim 15, wherein the actuator apparatus further comprises a spring member mounted between the plunger and the fitting to hold the plunger in a retracted position until a force is applied to slide the plunger distally with respect to the lilting.

18. The system of claim 15, further comprising an introducer adapted for insertion through the fitting lumen and the plunger lumen, the introducer including a lumen extending therethrough adapted to slidably receive the elongate injection apparatus, and wherein the elongate injection apparatus may be loaded into the fitting lumen and the plunger lumen of the apparatus by means of the introducer, which may be removed from the apparatus following loading.

19. The system of claim 15, wherein the distal portion of the shaft of the injection apparatus further includes a third segment extending distally between the proximal portion and the first segment, the spiral cut having a generally exponentially decreasing pitch along the third segment.

20. The system of claim 15, wherein the injection apparatus further comprises an outer layer extending over the spiral cut portion.

21. The system of claim 20, wherein the outer layer comprises a polymer.

22. The system of claim 15, wherein the length of the distal portion is between approximately 50 mm and approximately 500 mm long.

23. The system of claim 15, wherein the injection apparatus further comprises a grip tube positioned about the shaft in proximity to the shaft proximal end; the grip tube facilitating gripping by the means for reversibly gripping the injection apparatus within the plunger lumen.

24. The system of claim 15, wherein the injection apparatus further includes a fitting coupled to the proximal end of the shaft, the fitting adapted to connect the shalt to a source for injection of the therapeutic agents from the source through the injection apparatus.

25. A medical actuator apparatus, comprising:
a fitting for coupling the apparatus to a proximal portion of a delivery catheter, the fitting including a fitting lumen extending therethrough adapted to slidably receive an elongate member and to direct the elongate member through a lumen of the catheter;
a plunger slidably engaged with the fitting, the plunger including a plunger lumen extending therethrough adapted to slidably receive the elongate member and to direct the elongate member through the fitting lumen; the plunger further comprising a means for reversibly gripping the elongate member within the plunger lumen;
wherein the plunger slides distally with respect to the fitting to advance the elongate member within the catheter lumen when the apparatus is coupled to the catheter and the means for reversibly gripping the elongate member within the plunger lumen grips the elongate member; and
an introducer adapted for insertion through the fitting lumen and the plunger lumen, the introducer including a lumen extending therethrough adapted to slidably receive the elongate member, and wherein the elongate member may be loaded into the fitting lumen and the plunger lumen of the apparatus by the introducer, which is removed from the apparatus following loading.

* * * * *